(12) United States Patent
Bihler et al.

(10) Patent No.: US 11,504,506 B2
(45) Date of Patent: Nov. 22, 2022

(54) STRAIN SENSOR FOR A MEDICAL DEVICES WITH IMPROVED MEASUREMENT SENSITIVITY

(71) Applicant: DYCONEX AG, Bassersdorf (CH)

(72) Inventors: Eckardt Bihler, Winterthur (CH); Marc Hauer, Uster (CH)

(73) Assignee: Dyconex AG, Bassersdorf (CH)

( * ) Notice: Subject to any disclaimer, the term of this patent is extended or adjusted under 35 U.S.C. 154(b) by 725 days.

(21) Appl. No.: 16/432,291

(22) Filed: Jun. 5, 2019

(65) Prior Publication Data
US 2019/0366057 A1 Dec. 5, 2019

(30) Foreign Application Priority Data
Jun. 5, 2018 (DE) .......................... 102018208809.8

(51) Int. Cl.
*G01L 9/12* (2006.01)
*A61M 25/10* (2013.01)
*A61M 25/00* (2006.01)

(52) U.S. Cl.
CPC ............... *A61M 25/10* (2013.01); *G01L 9/12* (2013.01); *A61M 25/104* (2013.01); *A61M 2025/0002* (2013.01)

(58) Field of Classification Search
None
See application file for complete search history.

(56) References Cited

U.S. PATENT DOCUMENTS

| 7,610,089 | B1* | 10/2009 | Rodriguez | A61N 1/36514 310/317 |
| 8,066,650 | B2* | 11/2011 | Lee | A61B 5/14546 600/587 |
| 9,700,258 | B2* | 7/2017 | Jiang | A61F 2/80 |
| 2009/0320596 | A1* | 12/2009 | Classen | G01P 15/125 73/514.32 |
| 2010/0231207 | A1* | 9/2010 | Ogawa | G01L 1/14 324/209 |

(Continued)

FOREIGN PATENT DOCUMENTS

| DE | 2609130 A1 | 9/1977 |
| DE | 102006059928 A1 | 8/2008 |
| GB | 1201308 | 8/1970 |

*Primary Examiner* — Lisa M Caputo
*Assistant Examiner* — Nigel H Plumb
(74) *Attorney, Agent, or Firm* — Laurence A. Greenberg; Werner H. Stemer; Ralph E. Locher

(57) ABSTRACT

A strain sensor for capacitive strain measurement has a flat and electrically conductive first conductor element and a flat and electrically conductive second conductor element. The two conductor elements oppose one another and are laterally displaceable relative to one another, so that the two conductor elements, proceeding from a first condition, may be displaced relative to one another into a second condition. An overlap between the two conductor elements is different in the first condition from the second condition. First and second springs attach the conductor elements to first and second attaching regions of the strain sensor. The first attaching region is disposed at a first reference point of a body to be measured, and/or the second attaching region is disposed at a second reference point of the body to be measured.

17 Claims, 6 Drawing Sheets

(56) References Cited

U.S. PATENT DOCUMENTS

| | | | |
|---|---|---|---|
| 2015/0168236 A1* | 6/2015 | Bao | G01L 1/18 73/862.625 |
| 2016/0033343 A1* | 2/2016 | Park | G01L 1/146 73/862.046 |
| 2017/0059434 A1* | 3/2017 | Li | G01L 9/0072 |

* cited by examiner

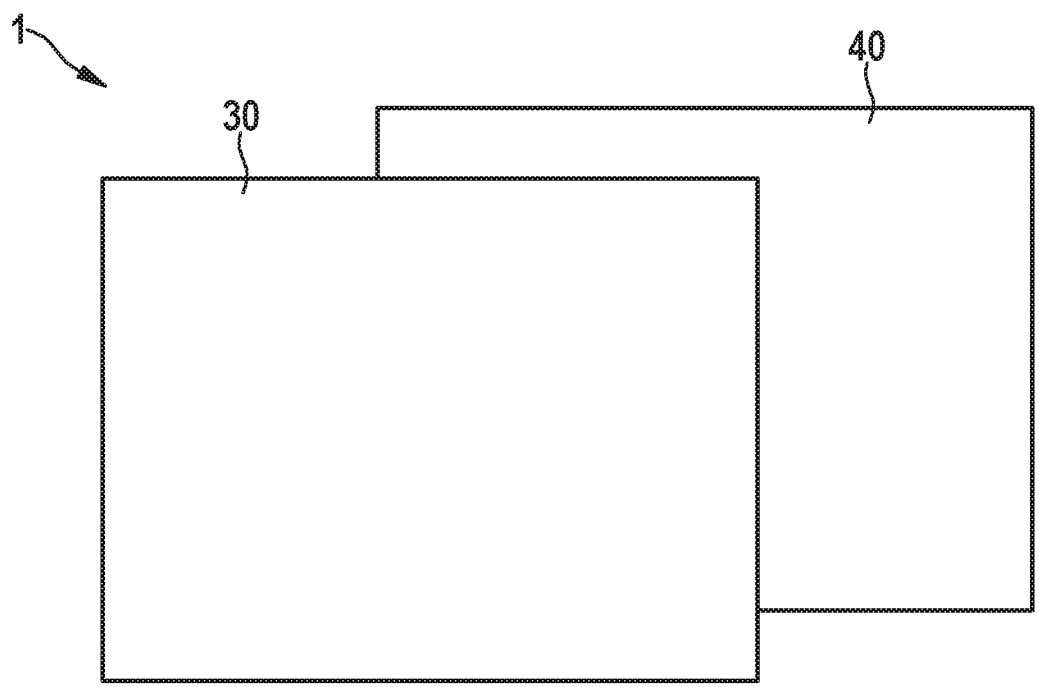
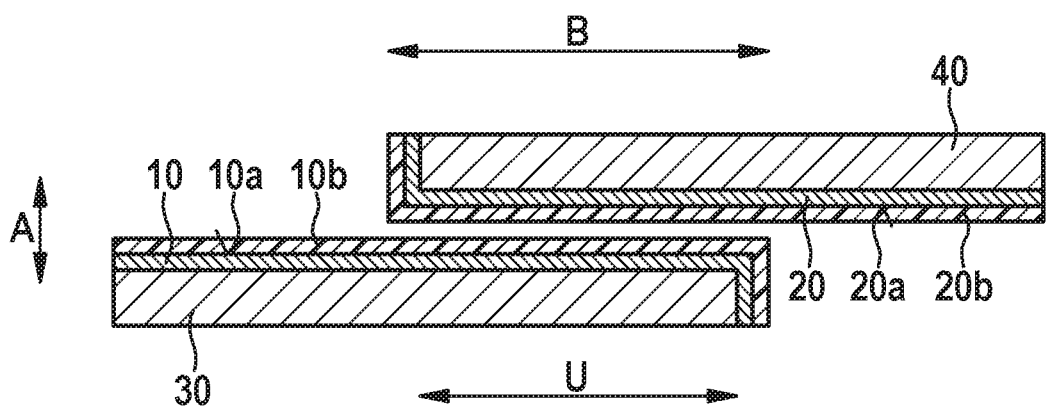
FIG. 1

STRAIN SENSOR FOR A MEDICAL DEVICES WITH IMPROVED MEASUREMENT SENSITIVITY

CROSS-REFERENCE TO RELATED APPLICATION

This application claims the priority, under 35 U.S.C. § 119, of German patent application DE 10 2018 208 809.8, filed Jun. 5, 2018; the prior application is herewith incorporated by reference in its entirety.

BACKGROUND OF THE INVENTION

Field of the Invention

The present invention relates to a strain sensor, in particular for a medical device, in particular for a balloon catheter, and to a balloon catheter having such a strain sensor.

Such strain sensors are known in the prior art, for example in the form of strain gauges that detect a change in the resistance of thin metal films during elastic extensions and compressions. Also known are travel sensors that work in a capacitive manner and that are used to detect the smallest changes in spacing between two metalized surfaces using a change in the electric capacitance.

Such known methods for measuring strain can regularly determine only relatively small extensions and compressions in a reproducible and precise manner. The relative extensions are in the range of a few percent. The sensing elements must be significantly thinner than the structure to be measured, so that the mechanical properties of the structure to be measured are not strongly influenced by the sensing elements. For the desired use of strain measurements in tissues and extensible films or tubes, the thickness of the sensing elements would have to be in the range of less than 1 µm, which is technically difficult and economically unattractive.

Balloon catheters are employed both for classic balloon angioplasty and for implanting plastically deformable implants such as stents. Classic balloon angioplasty, also known as "plain old balloon angioplasty" (POBA), expands the constricted blood vessel mechanically. If there is a high risk of relapse, after the vessel has been mechanically expanded it may be necessary to insert another balloon that is coated with medications. Likewise, it may be useful to use balloon angioplasty to widen a plastically deformable stent and thus to implant the latter in a constricted blood vessel. The implanted stent thus prevents the blood vessel from resiliently returning to its constricted state.

Such balloon catheters have at least one catheter shaft, the balloon being arranged at the distal end thereof. Furthermore, such balloon catheters have a lumen for a guide wire and a lumen for supplying an inflation medium (fluid) that expands the balloon (dilates the balloon). For implanting a plastically deformable stent, the latter, in a compressed form, is placed over the balloon and expanded by means of dilating the balloon and thus is anchored in the vessel. Such stents may also be formed of metal or polymer, either with or without a coating containing an active substance.

During a procedure, if the catheter is disposed at the desired location in the blood vessel, as a rule the balloon may be filled, and correspondingly expanded, at high pressure (up to 16 atm) with a fluid that contains a contrast agent. During an angioplasty, the calcium deposits are pressed into the vessel wall due to the strong pressure the balloon exerts on the vessel wall, and the diameter of the vessel enlarges. During such a procedure it is desirable, of course, that the treating physician can monitor the changing balloon diameter as precisely as possible as the balloon expands.

For determining or estimating the instantaneous diameter of the balloon in a balloon catheter, in the prior art it is known, e.g., to use the relationship, shown on a so-called compliance chart for the balloon catheter, between an inflation pressure applied to the balloon catheter or prevailing in the balloon interior and the diameter of the balloon. As a rule, the inflation pressure is measurable so that it is possible to estimate the corresponding diameter of the balloon therefrom.

Moreover, balloon catheters are known, the balloons of which have sensors on the balloon surface. Such sensors must be able to withstand a multiaxial strain of up to 30%. Repeatability of the measurement is also important, but as a rule is not provided by the viscoelastic property of the polymer balloon.

Furthermore, U.S. Pat. No. 8,066,650 B2 describes a capacitive sensor in which a number of fingers slide into one another and form a plurality of parallel capacitors. Due to the number of fingers that engage in one another, however, such a sensor arrangement is comparatively complex in design and requires appropriate installation space.

SUMMARY OF THE INVENTION

Proceeding herefrom, the underlying object of the present invention is therefore to provide an improved strain sensor that is suitable, in particular, for detecting greater strains (approx. 10%) in, e.g., flexible materials (non-wovens, rubber mats, tubes, etc.) having low hysteresis, good accuracy, and a long service life. The improved strain sensor should be embodied in particular for measuring the balloon diameter of a balloon catheter. A balloon catheter having such a strain sensor for precisely measuring the diameter of the balloon is a further object of the present invention.

With the above and other objects in view there is provided, in accordance with the invention, a strain sensor for capacitive strain measurement, the strain sensor comprising:
two conductor elements, including a flat and electrically conductive first conductor element and a flat and electrically conductive second conductor element;
the two conductor elements opposing one another and being disposed laterally displaceable relative to one another;
the two conductor elements, proceeding from a first condition, being displaceable into a second condition, wherein an overlap formed by the two conductor elements in the first condition is larger or smaller than in the second condition.

In other words, the objects of the invention are achieved with a strain sensor for capacitive measurement of an extension/compression of a body (e.g. a body of a medical device). The novel strain sensor has a flat and electrically conductive first conductor element and a flat and electrically conductive second conductor element, the two conductor elements opposing one another and being arranged laterally displaceable relative to one another, so that the two conductor elements, proceeding from a first condition, may be brought into a second condition, wherein an overlap formed by the two conductor elements is larger or smaller in the first condition than in the second condition.

According to one preferred embodiment, it is provided that the first conductor element is connected to a first attaching region of the strain sensor via a first spring element, and wherein the second conductor element is connected to a second attaching region of the strain sensor via a second spring element.

The elastic modulus (or E modulus, modulus of elasticity) of the strain sensor is defined with the spring elements. The E modulus may be precisely selected in a wide range using the selection of the dimensions of the spring element.

The conductor elements are significantly more rigid and have a significantly lower E modulus. The conductor elements are deformed to a much lesser degree than the spring element; because of this good linearity is attained between change in capacity and strain. The sensitivity of the sensor is provided by the change in capacity of the conductor elements relative to one another. The larger the surface areas and the smaller the spacing to one another, the more sensitive the sensor is.

A strain sensor without spring elements, if the conductor elements had the same dimensions, would be substantially more rigid and thus would also not be as sensitive. The E modulus of the entire sensor may be substantially reduced by adding the spring element, so that the sensitivity, and simultaneously also the linearity, of the strain sensor is enhanced considerably.

According to one preferred embodiment, it is provided that the first attaching region for attaching the strain sensor is embodied at a first reference point of a body to be measured, and/or that the second attaching region for attaching the strain sensor is embodied at a second reference point of the body to be measured. If the body is subjected to an extension or compression, the spacing between the two reference points changes accordingly. This change may be detected by means of the strain sensor.

The first reference point and the second reference point of the body to be measured are preferably disposed on the far side of the strain sensor in the direction of the extension of the body to be measured (along the movement direction B).

The two conductor elements are each in particular embodied flat along an extension plane and are arranged laterally displaceable relative to one another along the extension planes. According to one embodiment, the thickness of each conductor element normal to the specific extension plane is significantly less than the length and width of the conductor element in the extension plane. The thickness is in particular less than the width and/or length by a factor of 10, in particular by a factor of 100.

Both extensions (in which the overlap decreases in size) and compressions (in which the overlap increases in size) may be measured in a simple manner by means of the conductor elements due to the inventive configuration.

According to one embodiment it may be provided that the strain sensor has only two or exactly two conductor elements arranged above one another that are formed by the first conductor element and the second conductor element.

The two conductor elements form in particular a capacitor, the capacity of this capacitor being a function, inter alia, of how much the two conductor elements overlap one another. A change in the overlap is therefore measurable by measuring the capacity of the capacitor or a variable proportional thereto, which is possible by calculating the lateral displacement of the two conductor elements. The strain sensor has, in particular, an electronic circuit that is configured to determine the capacity or the aforesaid variable and thus to determine a corresponding displacement of the two conductor elements relative to one another. A number of methods are known from the prior art for this purpose. In particular the two conductor elements are each rigidly coupled to a reference point of a body, the extension of which is to be measured, so that the displacement of the two conductor elements relative to one another corresponds to a certain spacing between the two reference points. Thus an extension of the body, i.e., a change in the spacing between the two reference points, may be determined. The conductor elements are rigidly coupled to the reference points using the attaching regions, which are not connected to the conductor elements via spring element.

Using the invention, strain sensors may be realized that have good reproducibility for larger extensions, in particular in the two-digit percentage range. The strain sensors may in particular be integrated into tissue or other (in particular thin) extensible materials (e.g. polyurethane or silicone rubber films and tubes) without having too great an influence on the mechanical properties.

According to one embodiment of the inventive strain sensor, it is provided that the two conductor elements oppose one another in a spacing direction.

Moreover, according to one embodiment of the inventive strain sensor, it is provided that the spacing direction runs normal to a surface of the first conductor element and normal to a surface of the second conductor element.

Moreover, according to one embodiment of the inventive strain sensor, it is provided that the two surfaces oppose one another in the first condition (and thus in particular face one another) and/or run parallel to one another.

Since ideally the two conductor elements are to be in very close contact, it is desirable that they do not exchange any charge carriers. To this end, according to one embodiment it is provided that the two conductor elements are electrically insulated from one another.

In this regard, according to one embodiment of the inventive strain sensor it is provided that the two surfaces (facing one another) of the two conductor elements are each covered with an electric insulation. According to one embodiment, it is provided that the insulation has a thickness in the range of 1 nm to 10 µm in the spacing direction or normal to the specific surface. The advantage of the electrical insulation is that the two surfaces of the strain sensor may be disposed very close to or on one another and thus the measurement sensitivity may be enhanced.

In particular, the two electrical insulations of the aforesaid surfaces may be positioned against one another so that the two conductor elements may slide along one another with said insulations as an intermediate layer.

According to one embodiment of the invention, it is furthermore provided that each conductor element has a metal that embodies, on the surface of that conductor, an oxide layer that forms the associated electrical insulation.

The metal may be, e.g., titanium or aluminum. The thickness of such an insulation may be in the range of 10 nm to 100 nm, so that the measured capacities may be relatively high. The electrical insulation may also be formed by an organic film or an inorganic coating. The electrical insulation is preferably formed by a layer containing or comprising polyimide or LCP (liquid crystal polymer). The advantage of an insulation layer made of these substances is that even very thin layers of these substances have a high degree of electrical insulation. The strain sensor may thus be very thin without this having a negative impact on the strain measurement. Moreover, according to one embodiment of the inventive strain sensor it may be provided that the two conductor elements are arranged laterally displaceable relative to one another along a movement direction.

The movement direction may run perpendicular to the spacing direction and/or parallel to the two surfaces of the conductor elements.

Moreover, according to one preferred embodiment of the inventive strain sensor it is provided that the flat configuration of the two conductor elements means in particular that the two conductor elements each has a thickness in the spacing direction (or normal to the specific aforesaid surface), wherein the thickness of each conductor element is less than one length and/or one width of the specific conductor element along a plane perpendicular to the spacing direction (or less than one length and/or one width of the specific conductor element along the aforesaid surface of the specific conductor element). The aforesaid length of each conductor element extends in particular along the movement direction, while the width of each conductor element extends perpendicular to the movement direction. The width of each conductor element is preferably less than the length of that conductor element. This arrangement leads to enhanced measurement sensitivity for the strain sensor.

According to one embodiment it is provided that the aforesaid thickness of the specific conductor element is in the range of 100 nm to 10 µm, particularly preferably is between 0.5 µm and 5 µm.

According to one embodiment of the invention it is provided that the first conductor element and/or the aforesaid surface of the first conductor element is or are embodied in a rectangular shape. Analogously, in one embodiment it is provided that the second conductor element and/or the aforesaid surface of the second conductor element is or are embodied in a rectangular shape. The two conductor elements preferably have the same dimensions.

Moreover, according to one preferred embodiment of the inventive strain sensor it is provided that the first conductor element is arranged on a first substrate and/or that the second conductor element is arranged on a second substrate.

According to one embodiment, the two substrates may be arranged opposing one another in the spacing direction and laterally displaceable relative to one another along the movement direction, so that, starting from the first condition, the two conductor elements and the two substrates may be displaced relative to one another into the second condition, wherein the overlap formed by the two conductor elements in the first condition is greater or less than in the second condition (see above).

The substrates are also embodied in particular as flat elements. That is, each substrate has a thickness in the spacing direction that is preferably significantly less than one length and one width of that substrate along the extension plane of said surface of the conductor element carried by that substrate. According to one embodiment it is provided that the specific thickness D of the first substrate and of the second substrate is in a range of 10 µm to 0.25 mm. Thus the strain sensor is very thin and may easily be integrated, e.g., into a medical device with minimal effect on the mechanical properties of the device.

Moreover, according to one embodiment each conductor element may be embodied as a metallization applied to the associated substrate. The metallization and in particular the electrical insulation may be produced, e.g. using a thin film method (e.g. sputtering). In this way it is possible to produce each insulation in particular such that it is relatively thin, which can have a positive effect on the sensitivity and accuracy of the sensor.

Moreover, according to one embodiment of the inventive strain sensor, it may be provided that the first substrate and/or the second substrate has or have one of the following materials or is or are formed from one of the following materials: a plastic, polymer, liquid crystal polymer. Preferred materials are films made of polyimide, liquid crystal polymer, polyurethane. Liquid crystal polymers (LCP) are particularly preferred, in particular for applications of the strain sensor in medical electronic devices, since this material is highly biocompatible.

Moreover, according to one embodiment of the inventive strain sensor it is provided that the first substrate has a segment on which the first conductor element is arranged, wherein that segment is connected to the first attaching region of the strain sensor via the first spring element. Correspondingly, according to one embodiment it is preferably provided that the second substrate also has a segment on which the second conductor element is provided, wherein the second segment of the second substrate is connected to the second attaching region of the strain sensor via the second spring element. Each attaching region may also have, e.g., a loop or may be embodied, e.g., as a loop.

In accordance with one embodiment, the two spring elements are in particular configured such that they provide a restoring force that attempts to displace the two conductor elements out of the second condition back into the first condition.

Moreover, according to one embodiment of the inventive strain sensor it is provided that the first spring element is integrally joined to the aforesaid segment of the first substrate and/or that the second spring element is integrally joined to the aforesaid segment of the second substrate.

Similarly, according to one embodiment of the inventive strain sensor it may be provided that the first attaching region is integrally joined to the first spring element and/or that the second attaching region is integrally joined to the second spring element.

Each substrate may thus form, with the associated spring element and the associated attaching region, a uniform element or substrate molded from one piece.

Moreover, according to one embodiment of the invention it is provided that the first conductor element is joined to a third attaching region of the strain sensor, wherein the third attaching region for attaching the strain sensor is preferably embodied at the second reference point of the body to be measured, and/or that the second conductor element is joined to a fourth attaching region of the strain sensor, wherein the fourth attaching region for attaching the strain sensor is preferably embodied at the first reference point of the body to be measured.

Moreover, according to one embodiment of the invention it is provided that the aforesaid segment of the first substrate is joined to the third attaching region of the strain sensor, and/or that the aforesaid segment of the second substrate is joined to the fourth attaching region of the strain sensor. Again, it is in particular provided that the aforesaid segment of the first substrate is integrally joined to the third attaching region of the strain sensor. Moreover, it is in particular provided that the aforesaid segment of the second substrate is integrally joined to the fourth attaching region of the strain sensor.

Each substrate may thus form, with the associated spring element and the associated attaching regions, a uniform element or substrate molded from one piece.

Moreover, according to one embodiment the third attaching region is arranged such that the first conductor element and the first spring element are arranged between the first attaching region and the third attaching region. Correspondingly, according to one embodiment the fourth attaching region is furthermore arranged such that the second conductor element and the second spring element are arranged between the second attaching region and the fourth attaching region.

The inventive strain sensor thus in particular has two components or basic elements that each have a conductor, a spring element, and two attaching regions (see above).

According to one embodiment of the invention, in this regard it is preferably provided that the first attaching region and the fourth attaching region are arranged above one another and fixed to one another, and that the second attaching region and the third attaching region are arranged above one another and fixed to one another, so that the two spring elements are prestressed when the first attaching region and the fourth attaching region are attached at a first reference point and the second attaching region and the third attaching region are attached at the second reference point of the body to be measured and the two conductor elements are displaced or moved relative to one another out of the first condition into the second condition by a change in the spacing between the reference points (e.g. due to an extension or compression of the body).

The third attaching region and the fourth attaching region may also each have a loop or may also each be embodied as a loop. Then one attaching element may be passed through each of the loops, which are disposed above one another, in order to fix the strain sensor at two reference points of the body so that it is possible to measure a change in the spacing between the two reference points (due to an extension of the body) by means of the strain sensor. The attaching regions may also be embodied in another fashion, of course. It also possible to join the attaching regions to one another or to the body to be measured, e.g. in a material fit.

Moreover, according to one embodiment of the invention it is provided that each spring element has a winding course and a plurality of winding arcs and segments that connect to one another, wherein in this case an extension of the spring element corresponds to an expansion in the individual winding arcs or segments of the spring.

According to one embodiment the strain sensor may have a guide in order to furthermore assure that the two conductor elements or the two substrates can each move only along a defined axis, i.e., along the movement direction. The guide may have, for example, a groove-like opening in both substrates and each of the latter may have a guide pin inserted therein.

Since the measured capacity furthermore depends not only on the overlap of the capacitive conductor elements, but is also is influenced by their spacing, spacing between the two conductor elements or between the surfaces of the conductor elements that face one another is kept constant in the spacing direction.

Therefore, according to one embodiment of the invention it is provided that the strain sensor has a cuff that holds the conductor elements together in the spacing direction. In this way it is possible in particular to reduce the spacing between the two substrates or conductor elements to a minimum.

Moreover, according to one embodiment of the invention it is provided that the strain sensor has a liquid film between the two conductor elements. The spacing between the surfaces may be adjusted in a defined manner by means of this liquid, due to corresponding capillary forces, which liquid coats both insulated surfaces of the conductor elements. One advantage of this embodiment is that the friction between two conductor elements is minimized by the liquid film.

To further minimize a thickness of the strain sensor, according to a further embodiment it may be provided that the two conductor elements are charged electrostatically during operation of the strain sensor. Because of this, a force forms that draws the two conductor elements or surfaces together. Measuring the capacity may be set up such that it is not disturbed by this offset potential.

In the present invention, the capacitive conductor elements are preferably rectangular so that a linear relationship results between the position and the measured capacity results. For certain applications, however, a non-linear relationship may be advantageous. Such a relationship may be attained, e.g., using a specific shape of the conductor elements or surface contours.

Moreover, according to one embodiment of the invention it is provided that the strain sensor has a length in the range of 3 mm to 30 mm along the movement direction. Moreover, according to one embodiment, the strain sensor may have a width in the range of 0.5 mm to 5 mm perpendicular to the movement direction (and perpendicular to the spacing direction).

Another aspect of the present invention relates to a medical device having at least one inventive strain sensor and having an extensible body, wherein the strain sensor is configured to measure an extension and/or compression of the body.

According to one embodiment, the strain sensor is fixed to a first reference point of the body via the first attaching region and the fourth attaching region (see above, in particular). Moreover, according to one embodiment the strain sensor is fixed to a second reference point of the body via the second attaching region and the third attaching region (see above, in particular).

The medical device may in particular be a catheter device, wherein the aforesaid body may be a segment of a catheter shaft of the catheter device, for example. Other medical devices, such as, e.g., implanted electrodes or implantable monitors for detecting extensions and compressions in the body are also possible, however. The inventive strain sensor has particular advantages for these applications due to the biocompatible and biostable materials that are used for the strain sensor. Another particular advantage is found in the low E modulus, which results from the inventive structure and the large relative extensions and compressions that may be detected with the inventive structure. Previously known sensors have far greater rigidity and are therefore only suitable for measuring smaller relative extensions.

According to one embodiment of the invention of the inventive medical device, it may also be provided that the strain sensor is integrated in the aforesaid body, i.e., is embedded in the body to be measured, that is, e.g. is enclosed thereby. This is possible because, compared to known strain sensors, the inventive strain sensor is particularly thin and thus does not influence the mechanical properties of the device or only influences them in certain circumstances. This is particularly important for medical devices such as catheter tubes or catheter balloons. The thickness of such medical devices must be kept as low as possible so that there is no negative effect on the ability to insert them into the body of the patient and to control them in the body. Due to their thin embodiment and minimal effect on bendability, the inventive strain sensors may therefore be used advantageously in such devices.

A balloon catheter having a strain sensor like the embodiments described in the foregoing is also in accordance with the invention.

An inventive balloon catheter has at least one catheter shaft, the balloon being arranged at the distal end thereof. Furthermore, an inventive balloon catheter has a lumen for a guide wire and a lumen for supplying an inflation medium (fluid) that expands the balloon (dilates the balloon).

Optionally, a plastically deformable stent in a compressed form is arranged on the balloon and may be expanded by means of balloon dilation. Such stents may be embodied preferably from metal or polymer as well as with or without a coating containing an active substance.

The strain sensor is preferably arranged on the inner or outer surface of the balloon. In one alternative embodiment, the strain sensor may also be embedded in the balloon. In either case, however, it is useful to arrange the strain sensor on the balloon such that the first reference point and the second reference point lie on a circumferential line of the balloon.

Other features which are considered as characteristic for the invention are set forth in the appended claims.

Although the invention is illustrated and described herein as embodied in a strain sensor, in particular for a medical device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

FIG. 1 illustrates the functional principle for the change in capacitance when electrically insulated conductor elements positioned above one another are displaced;

DETAILED DESCRIPTION OF THE INVENTION

Figure 2:
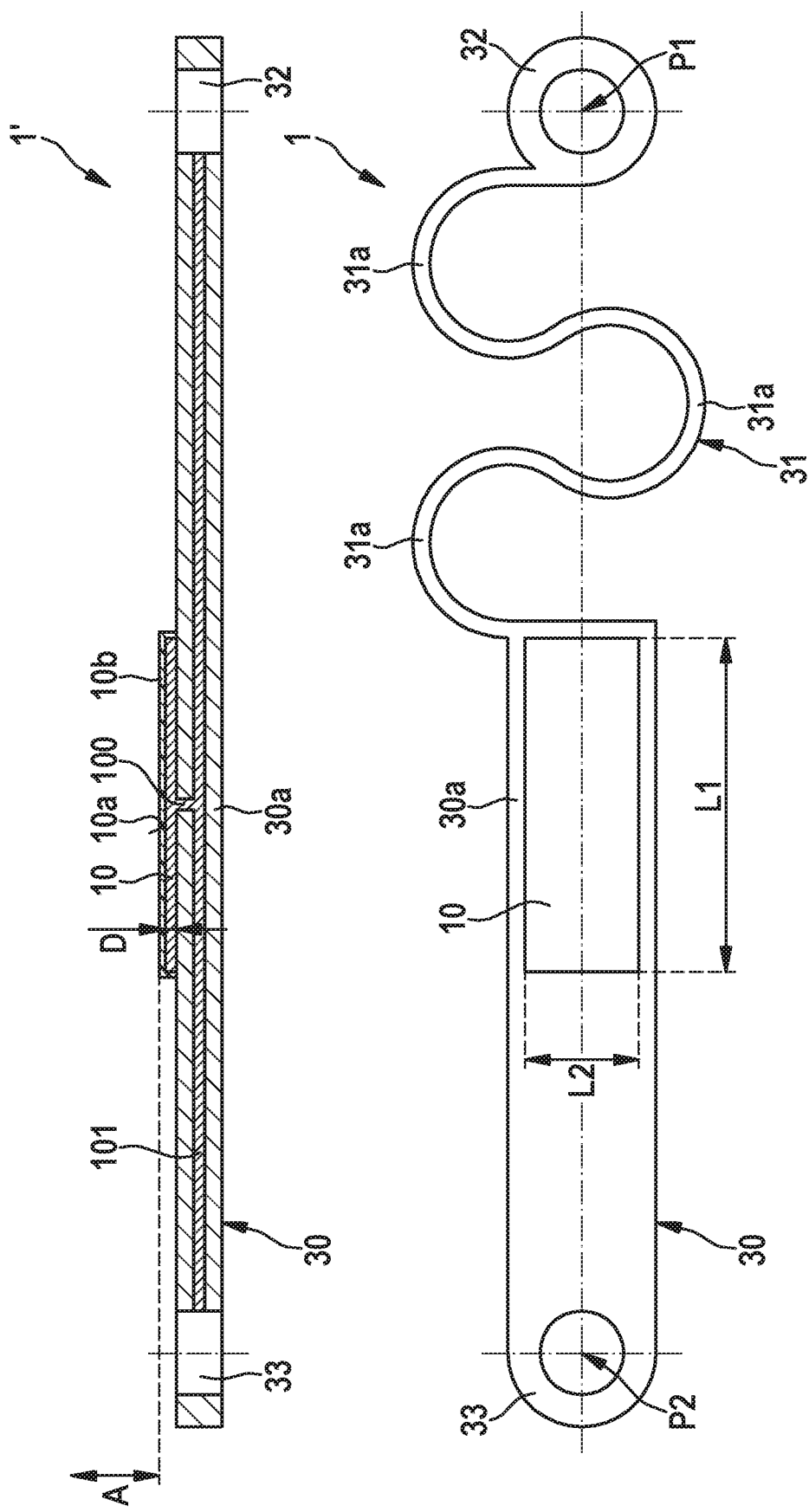
FIG. 2 illustrates an elementary basic element of one embodiment of an inventive strain sensor having a conductor element, a substrate, a spring element, and two attaching regions.

The present invention relates to a strain sensor 1 for capacitive strain measurement, in particular for measuring an extension/compression of a body 3 of a medical device (e.g. catheter or patch). The fundamental principle of the invention is illustrated in FIG. 1 and is based on the change in the electrical capacity of a capacitor that is formed by two opposing, laterally displaceable conductor elements 10, 20. The capacity of the capacitor changes due to the lateral displacement, wherein it is possible to measure the change or the specific capacity in a known manner by means of a suitable electronic circuit (not shown in greater detail here) in the strain sensor 1.

Referring now to the figures of the drawing in detail and first, particularly, to FIG. 1 thereof, there is shown the inventive strain sensor 1 with at least one flat and electrically conductive first conductor element 10 and one flat and electrically conductive second conductor element 20. The two conductor elements 10, 20 are arranged opposing one another and laterally displaceable relative to one another, so that the two conductor elements 10, 20, proceeding from a first condition relative to one another, may be displaced or brought into a second condition relative to one another. An overlap U that is formed by the two conductor elements 10, 20 is greater in the first condition (extension) or smaller (compression) than in the second condition.

According to FIG. 2, each conductor element 10, 20, in this case illustrated using the first conductor element 10, may be applied to a segment 30a of a substrate 30, which may comprise, e.g., a polymer film (e.g. polyimide, liquid crystal polymer, etc.), wherein the substrate 30 may have a thickness of 10 μm to 0.25 mm. The conductor element 10 may be formed, e.g., by a metalized surface that may have a thickness D, e.g. in the range of 100 nm to 10 μm. A surface 10a of the conductor element 10 may be covered with an electrical insulation that may have a thickness, e.g. in the range of 1 nm to 10 μm. The metallization or the conductor element 10 and the insulation 10b are preferably produced with a thin-film method (e.g. sputtering), so that the insulation layer in particular is as thin as possible. This influences the sensitivity and accuracy of the sensor 1.

The connection of the segment 30a to a first attaching region 32, which may be fixed at a first reference point P1 of a body 3 to be measured, is formed, e.g., from a winding strip 31, cutout as thin as possible, that forms a first easily extensible spring element 31 that has a plurality (in this case, e.g., three) winding arcs 31a connected to one another. The connection to the third attaching region 33, which may be fixed to a second reference point P2 of the body 3, is embodied, e.g., in the form of a wide strip that is thus only slightly extensible.

The leads (conductor tracks) 101 to the first conductor element 10 run, e.g., on a back side of the substrate 30 or polymer film 30 and may be covered with a further polymer film or a lacquer. The leads 100 may be connected in an electrically conducting manner to the first conductor element 10 by means of a through-connection (e.g. VIA).

Figure 3:
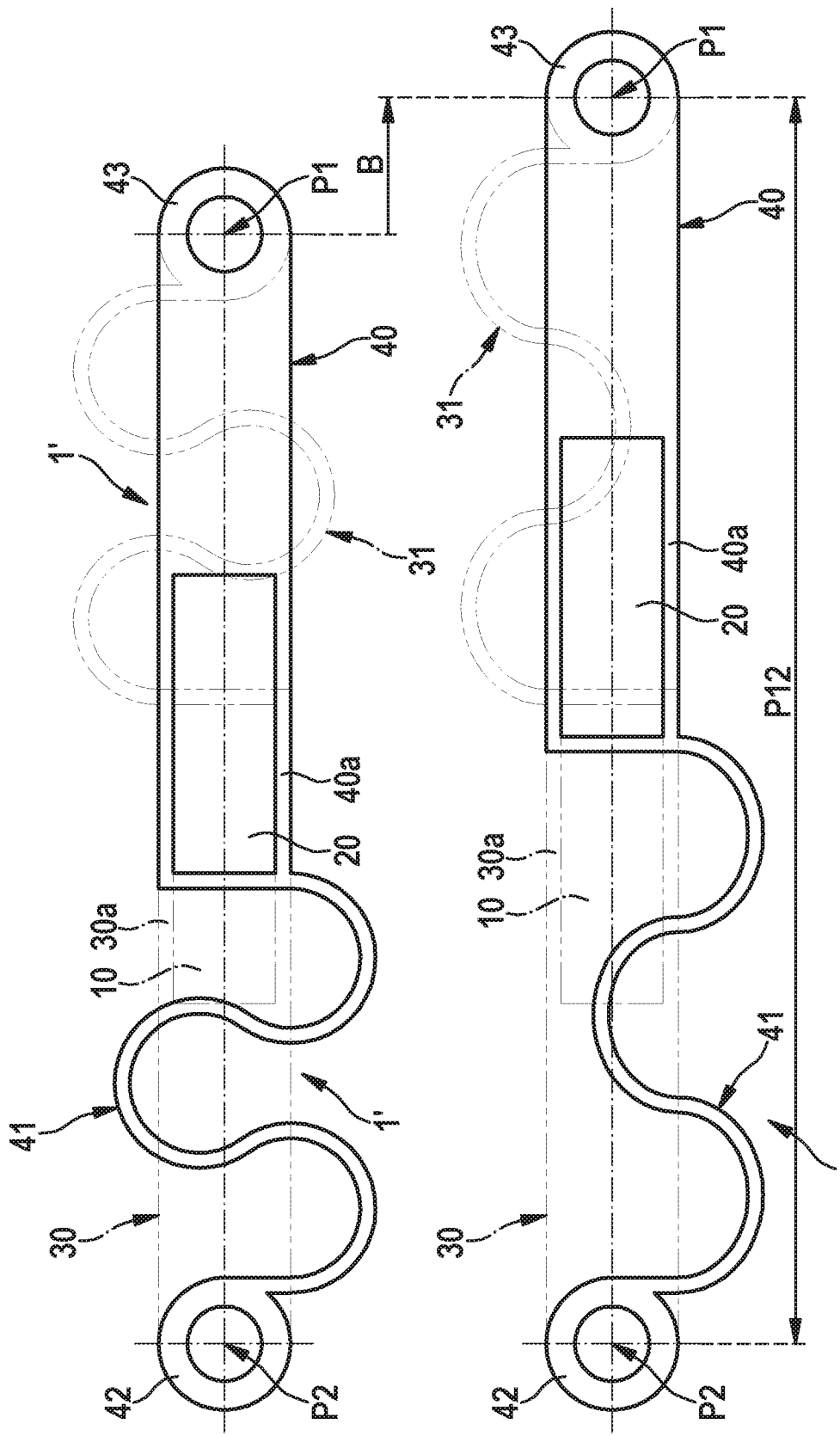
FIG. 3 illustrates the two conducting elements, positioned above one another, of one embodiment of an inventive strain sensor in the first condition and in the second condition.

The second conductor element 20 (see. FIG. 3) is arranged in the same manner on a segment 40a of a second substrate 40 that has a second spring element 41 and a second and a fourth attaching region 42, 43. The two conductor elements 10, 20 are thus in particular each components of a basic element 1' of the strain sensor 1. Each basic element 1' has the substrate 30 or 40, a spring element 31 or 41 (in particular with winding arcs 31a or 41a), and two attaching regions 32, 33 or 42, 43.

If the surfaces 10a, 20a of the conductor elements 10, 20 of two of these structures or basic elements 1' are now rotated 180° and placed against one another (see in particular FIGS. 3 and 4) and are connected at the attaching regions 33, 42 or 32, 43, which are now above one another and may be embodied, e.g., as loops, the result is a capacitive strain sensor 1 having the aforesaid reference points P1, P2 of the body 3 (see 4).

The two aforesaid basic elements 1' of the strain sensor 1 are securely connected to one another, in particular only in the region of the reference points P1, P2. Thus the extension of the material or body 3 to be measured is recorded at the reference points P1, P2.

Otherwise, the two basic elements 1' may move freely towards one another and along the movement direction B, the conductor elements 10, 20 being displaced laterally towards one another. Such displacement is produced in particular when the relative spacing between two reference points P1, P2 of the body 3 to be measured changes due to an extension or compression of the body 3 (see, e.g. FIG. 3).

The loops or attaching regions 33, 42 or 32, 43 may also be used to connect the conductor tracks 100, 200 to the circuit with a wire or in another manner to measure the capacity (e.g. LCR measuring bridge). To this end, corresponding contacts 50, 51 may be arranged between the adjacent loops or attaching regions 33, 42 and 32, 43, and may provide the leads 100 and 200 electrical contacting (see FIG. 4).

Figure 4:
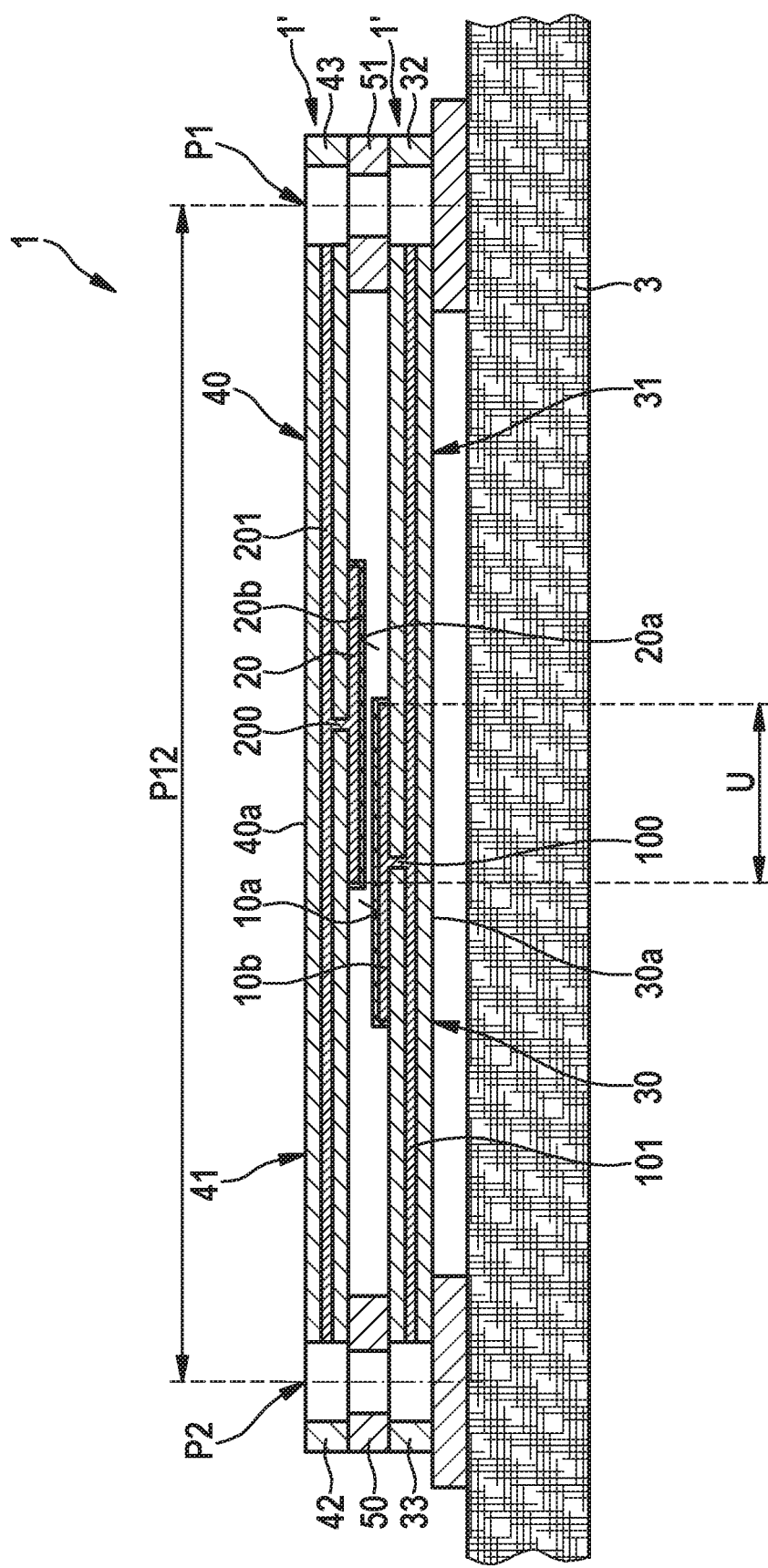
FIG. 4 is a schematic sectional view of one embodiment of an inventive strain sensor.

According, e.g., to FIG. 4, the body 3 may be an extensible tissue 3 or an extensible film 3. The strain sensor 1 and the body 3 may be connected in various manners. However, the strain sensor 1 is preferably fixed only to the reference points P1, P2 on the body or tissue 3 and otherwise may move freely. The strain sensor 1 may also be positioned between two tissues or films 3 or between two material layers.

The elasticity modulus of the strain sensor 1 is determined in particular by the spring elements 31, 41. The finer the latter are embodied, the smaller the E modulus becomes. The smaller the E modulus of the sensor 1, the higher the measuring sensitivity.

One inventive strain sensor 1 may be fixed in different fashions to a body 3 to be measured (depending on the extension to be measured) via the attaching regions 32, 33, 42, 43.

Figure 5:
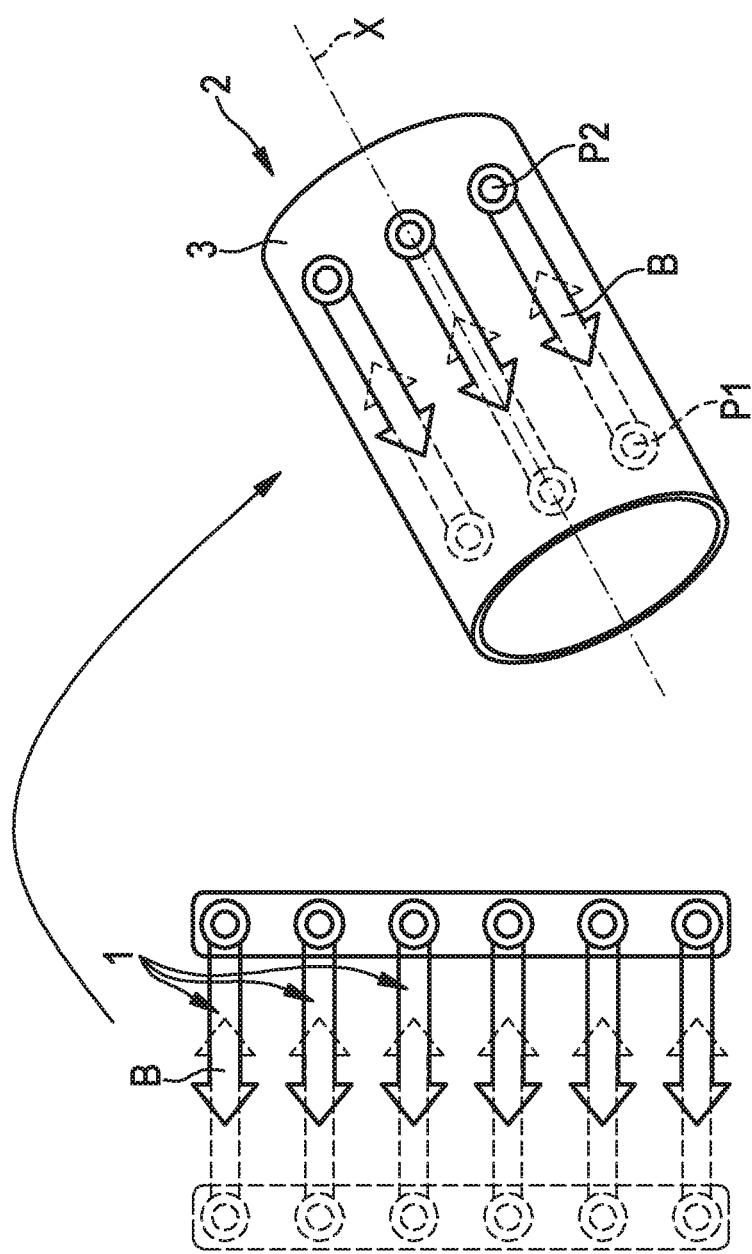
FIG. 5 illustrates an arrangement of a plurality of inventive strain sensors on a tube-like element for measuring an extension or bending of the tube-like element.

FIG. 5 depicts an arrangement with which the bending of a catheter shaft 3 of a catheter 2 may be measured. In this case, a plurality of inventive strain sensors 1 are arranged adjacent to one another in a circumferential direction of the catheter shaft 3 or body 3, the movement direction B of each strain sensor 1 running parallel to the longitudinal axis x of the shaft 3 (i.e., the first and second reference points P1, P2 oppose one another in the axial direction x). When the catheter shaft 3 is bent, the conductor elements 10, 20 are pressed together on one side of the shaft 3 and the overlap U increases there (see FIG. 1), while on the other side they are pulled apart from one another so that the overlap U decreases there. The capacities or output signals of the individual strain sensors 1 therefore permit the curvature of the shaft 3 to be determined precisely. Other medical devices having two or more inventive strain sensors also constitute part of the invention. A plurality of strain sensors in a medical device permits better determination of the extension or deformation of the device or part of the device.

Figure 6:
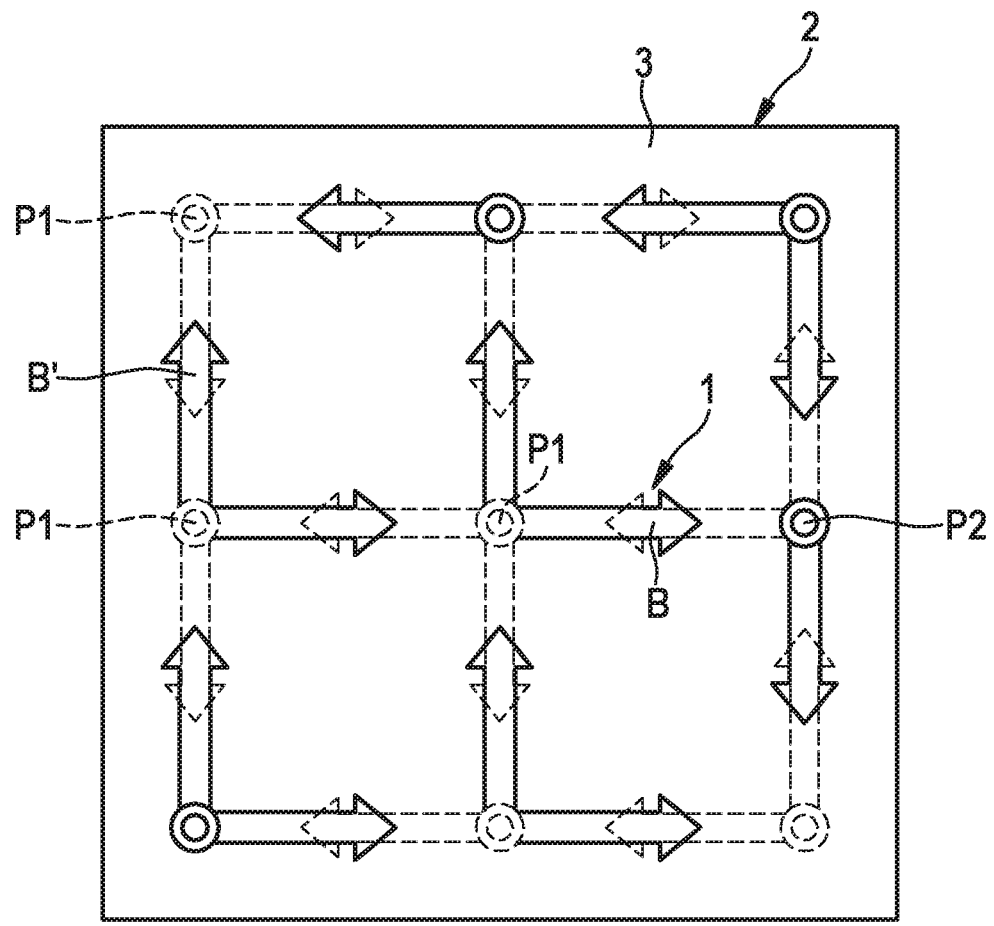
FIG. 6 illustrates a plurality of inventive strain sensors in one plane for detecting extensions between adjacent reference points of a square grid extending along the plane.

In contrast to FIG. 5, FIG. 6 depicts a flat arrangement of the strain sensors 1, so that the reference points P1, P2 are disposed on the nodes of a square grid. This permits determination of the extension/compression along two orthogonal movement directions B, B' in the plane illustrated.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. A strain sensor for capacitive strain measurement, the strain sensor comprising:
   two conductor elements, including a flat and electrically conductive first conductor element and a flat and electrically conductive second conductor element;
   said two conductor elements opposing one another and being disposed laterally displaceable relative to one another;
   said two conductor elements, proceeding from a first condition, being displaceable into a second condition, wherein an overlap formed by said two conductor elements in the first condition is larger or smaller than in the second condition;
   a first spring element connecting said first conductor element to a first attaching region of the strain sensor;
   a second spring element connecting said second conductor element to a second attaching region of the strain sensor; and
   wherein the first attaching region for attaching the strain sensor is disposed at a first reference point of a body to be measured; and/or
   wherein the second attaching region for attaching the strain sensor is disposed at a second reference point of the body to be measured.

2. The strain sensor according to claim 1, wherein said two conductor elements are positioned opposing one another in a spacing direction.

3. The strain sensor according to claim 1, which comprises a liquid film between said two conductor elements.

4. The strain sensor according to claim 1, wherein said two conductor elements may be charged electrostatically during an operation of the strain sensor.

5. The strain sensor according to claim 1, wherein each conductor element has a metal that forms an oxide layer on a surface of said conductor element.

6. The strain sensor according to claim 1, wherein said two conductor elements have surfaces facing one another and said are covered with an electrical insulation.

7. The strain sensor according to claim 6, wherein said electrical insulation is an organic film or an inorganic coating.

8. The strain sensor according to claim 1, wherein said first conductor element is joined to a third attaching region of the strain sensor, and/or said second conductor element is joined to a fourth attaching region of the strain sensor.

9. The strain sensor according to claim 8, wherein the third attaching region for attaching the strain sensor is disposed at the second reference point of the body to be measured, and/or the fourth attaching region for attaching the strain sensor is embodied at the first reference point of the body to be measured.

10. The strain sensor according to claim 8, wherein the first attaching region and the fourth attaching region are arranged above one another and fixed to one another, and wherein the second attaching region and the third attaching region are arranged above one another and fixed to one another, such that the two spring elements are prestressed when the first attaching region and the fourth attaching region are attached at a first reference point and the second attaching region and the third attaching region are attached at the second reference point and the two conductor elements are displaced out of the first condition into the second condition by a change in a spacing between the reference points.

11. The strain sensor according to claim 1, wherein said first conductor element is arranged on a first substrate and/or said second conductor element is arranged on a second substrate.

12. A medical device, comprising a body and at least one strain sensor according to claim 1, wherein said strain sensor is configured for measuring at least one of an extension or compression of said body.

13. A balloon catheter, comprising a balloon with a strain sensor according to claim 1.

14. A strain sensor for capacitive strain measurement, the strain sensor comprising:
- two conductor elements, including a flat and electrically conductive first conductor element and a flat and electrically conductive second conductor element;
- said two conductor elements opposing one another and being disposed laterally displaceable relative to one another;
- said two conductor elements, proceeding from a first condition, being displaceable into a second condition, wherein an overlap formed by said two conductor elements in the first condition is larger or smaller than in the second condition; and
- wherein said two conductor elements are positioned opposing one another in a spacing direction, each of said two conductor elements has a thickness in the spacing direction, and the thickness of each conductor element is less than one length and one width of the respective said conductor element along a plane perpendicular to the spacing direction, and wherein the thickness is in a range between 100 nm and 10 μm.

15. The strain sensor according to claim 14, further comprising: a first spring element connecting said first conductor element to a first attaching region of the strain sensor; a second spring element connecting said second conductor element to a second attaching region of the strain sensor; and wherein the first attaching region for attaching the strain sensor is disposed at a first reference point of a body to be measured; and/or wherein the second attaching region for attaching the strain sensor is disposed at a second reference point of the body to be measured.

16. A strain sensor for capacitive strain measurement, the strain sensor comprising:
- two conductor elements, including a flat and electrically conductive first conductor element and a flat and electrically conductive second conductor element;
- said two conductor elements opposing one another and being disposed laterally displaceable relative to one another;
- said two conductor elements, proceeding from a first condition, being displaceable into a second condition, wherein an overlap formed by said two conductor elements in the first condition is larger or smaller than in the second condition;
- wherein said first conductor element is arranged on a first substrate and/or said second conductor element is arranged on a second substrate, and wherein:
- said first substrate has a first segment on which said first conductor element is arranged, and said first segment of said first substrate is connected to said first attaching region of the strain sensor via said first spring element; and/or said second substrate has a second segment on which said second conductor element is arranged, and said second segment of said second substrate is connected to said second attaching region of the strain sensor via said second spring element.

17. The strain sensor according to claim 16, wherein said first segment is connected to said third attaching region of the strain sensor and/or said second segment is connected to said fourth attaching region of the strain sensor.

* * * * *